(12) United States Patent
Araldi et al.

(10) Patent No.: US 7,511,150 B2
(45) Date of Patent: Mar. 31, 2009

(54) SYNTHESIS OF HETEROCYCLIC COMPOUNDS

(75) Inventors: Gian-Luca Araldi, East Setauket, NY (US); Melanie Ronsheim, Port Jefferson, NY (US); Nhut Diep, Hauppauge, NY (US); Shao Hong Zhou, Commack, NY (US)

(73) Assignee: Forest Laboratories Holdings Limited (BM)

( * ) Notice: Subject to any disclaimer, the term of this patent is extended or adjusted under 35 U.S.C. 154(b) by 0 days.

(21) Appl. No.: 11/772,863

(22) Filed: Jul. 3, 2007

(65) Prior Publication Data

US 2008/0009632 A1 Jan. 10, 2008

Related U.S. Application Data

(60) Provisional application No. 60/806,649, filed on Jul. 6, 2006.

(51) Int. Cl.
*C07D 407/12* (2006.01)
(52) U.S. Cl. .................................. 546/284.1
(58) Field of Classification Search ............... 546/284.1
See application file for complete search history.

(56) References Cited

U.S. PATENT DOCUMENTS

| 7,223,789 B2 | 5/2007 | Gopalan et al. |
| 7,238,725 B2 | 7/2007 | Balasubramanian et al. |
| 2006/0135779 A1 | 6/2006 | Gopalan et al. |

FOREIGN PATENT DOCUMENTS

| WO | WO 2004/069831 | 8/2004 |
| WO | WO 2004/089940 | 10/2004 |
| WO | WO 2004/111044 | 12/2004 |

OTHER PUBLICATIONS

International Search Report for PCT/US2007/72696, mailed Jul. 29, 2008.
Written Opinion of the International Searching Authority for PCT/US2007/72696, mailed Jul. 29, 2008.

*Primary Examiner*—Patricia L Morris
(74) *Attorney, Agent, or Firm*—Michael Ciraolo, Esq.; Jonathan Paul Mitchell

(57) ABSTRACT

Methods for the synthesis of heterocyclic compounds including N-(3,5-dichloropyrid-4-yl)-4-difluoromethoxy-8-methanesulfonamido-dibenzo[b,d]furan-1-carboxamide and pharmaceutically acceptable salts thereof.

18 Claims, 1 Drawing Sheet

Zinc Reduction

Raney-Nickel Reduction

Indium Reduction

SYNTHESIS OF HETEROCYCLIC COMPOUNDS

This application claims the benefit of U.S. Provisional Application Ser. No. 60/806,649, filed Jul. 6, 2006, the entire disclosure of which is hereby incorporated by reference.

FIELD OF THE INVENTION

The present invention relates to methods for the synthesis of heterocyclic compounds including N-(3,5-dichloropyrid-4-yl)-4-difluoromethoxy-8-methanesulfonamido-dibenzo[b,d]furan-1-carboxamide and pharmaceutically acceptable salts thereof.

BACKGROUND OF THE INVENTION

Phosphodiesterases ("PDEs") are a family of enzymes involved in regulating intracellular signalling. PDEs act by cleaving the intracellular second messengers cyclic AMP ("cAMP") and cyclic GMP ("cGMP"). Among the PDEs, PDE IV is the major cAMP metabolizing enzyme found in inflammatory and immune cells. PDE IV inhibitors have been investigated as anti-inflammatory treatments in airway diseases, including the treatment of asthma and chronic obstructive pulmonary disease (COPD).

U.S. patent application Ser. No. 10/821,642 (the '642 application), published as Publication No. 2005/0027129, discloses novel heterocyclic compounds for use as PDE IV inhibitors, the disclosure of which is incorporated by reference in its entirety. In addition, the '642 application discloses a multi-step synthesis of N-(3,5-dichloropyrid-4-yl)-4-difluoromethoxy-8-methanesulfonamido-dibenzo[b,d]furan-1-carboxamide and the corresponding sodium salt. One such compound is N-(3,5-dichloropyrid-4-yl)-4-difluoromethoxy-8-methanesulfonamido-dibenzo[b,d]furan-1-carboxamide sodium salt, represented by the following formula:

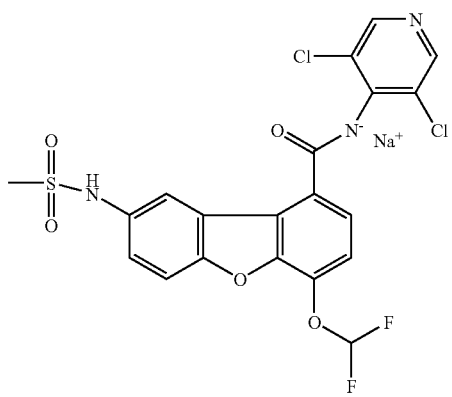

International Publication No. WO 2006/040652 also discloses methods for preparing N-(3,5 dichloropyrid-4-yl)-4-difluoromethoxy-8-methanesulfonamido-dibenzo[b,d]furan-1-carboxamide and its sodium salt, the disclosure of which is incorporated by reference in its entirety.

However, there remains a need in the art to provide methods for the synthesis of N-(3,5-dichloropyrid-4-yl)-4-difluoromethoxy-8-methanesulfonamido-dibenzo[b,d]furan-1-carboxamide and pharmaceutically acceptable salts thereof.

SUMMARY OF THE INVENTION

The present invention relates to methods for the synthesis of heterocyclic compounds including N-(3,5-dichloropyrid-4-yl)-4-difluoromethoxy-8-methanesulfonamido-dibenzo[b,d]furan-1-carboxamide and pharmaceutically acceptable salts thereof.

According to some embodiments, the present invention provides methods for preparing a substituted nitrophenoxy benzaldehyde of formula (c) comprising reacting a substituted benzaldehyde of formula (a) with a substituted nitrobenzene of formula (b):

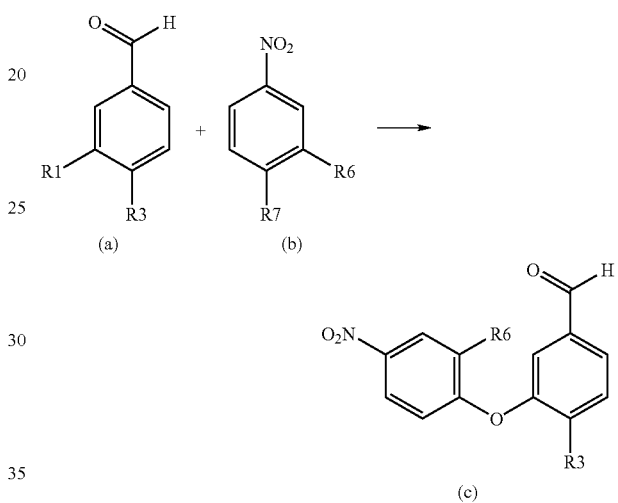

wherein R1 is selected from the group consisting of O, OH, and OR2; R2 is a substituted or unsubstituted alkyl; R3 is selected from the group consisting of H, OH, halogen, and O—CHR4R5, wherein R4 and R5 are each independently selected from the group consisting of H, OH, and halogen; and R6 and R7 are each independently selected from the group consisting of H, OH, and halogen.

According to other embodiments, the present invention provides compounds of formula I:

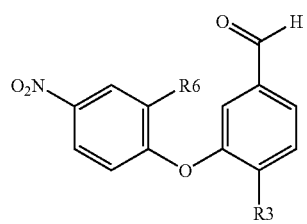

and physiologically acceptable salts thereof wherein R3 is selected from the group consisting of H, OH, halogen, and O—CHR4R5, wherein R4 and R5 are each independently selected from the group consisting of H and halogen; and R6 is selected from the group consisting of H, OH, and halogen.

According to other embodiments, the present invention provides methods of preparing a substituted dibenzofuran of formula (d) comprising cyclization of a substituted nitrophenoxy benzaldehyde of formula (c):

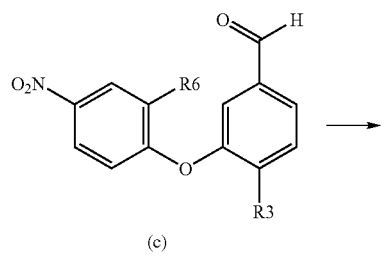

(c)

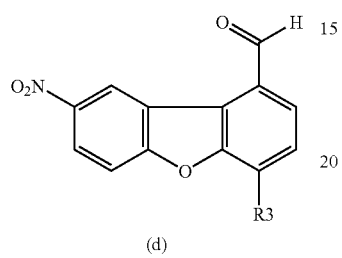

(d)

wherein R3 is selected from the group consisting of H, OH, halogen, and O—CHR4R5, wherein R4 and R5 are each independently selected from the group consisting of H, OH and halogen; and R6 is selected from the group consisting of H, OH, and halogen.

According to other embodiments, the present invention provides methods for preparing a substituted carboxylic acid of formula (e) comprising oxidizing a substituted dibenzofuran of formula (d):

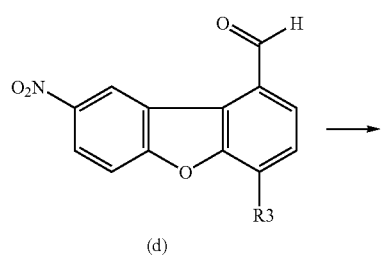

(d)

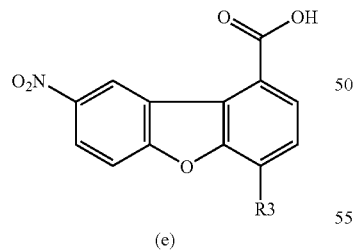

(e)

wherein R3 is selected from the group consisting of H, OH, halogen, and O—CHR4R5, wherein R4 and R5 are each independently selected from the group consisting of H, OH and halogen.

According to other embodiments, the present invention provides methods for preparing a substituted carboxylic acid of formula (e) comprising oxidizing a substituted dibenzofuran of formula (d):

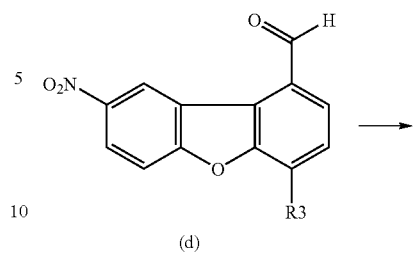

(d)

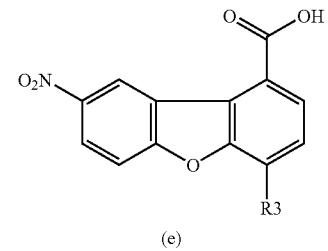

(e)

wherein R3 is selected from the group consisting of H, OH, halogen, and O—CHR4R5, wherein R4 and R5 are each independently selected from the group consisting of H, OH and halogen.

According to other embodiments, the present invention provides methods of preparing a substituted carboxamide of formula (g) comprising reacting a substituted carboxylic acid of formula (e) with a substituted aminopyridine of formula (f):

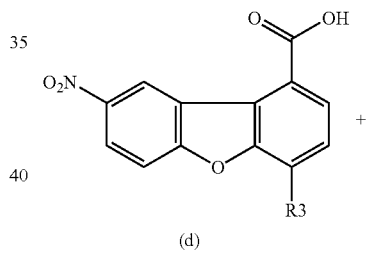

(d)

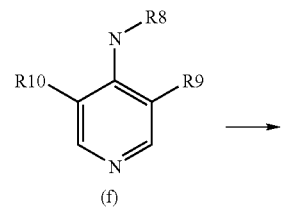

(f)

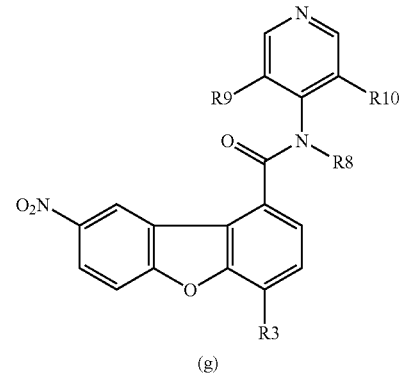

(g)

wherein R3 is selected from the group consisting of H, OH, halogen, and O—CHR4R5, wherein R4 and R5 are each independently selected from the group consisting of H, OH and halogen; R8 is selected from the group consisting of H and alkyl; and R9 and R10 are each independently selected from the group consisting of H, OH and halogen.

According to other embodiments, the present invention provides methods of preparing N-(3,5-dichloropyrid-4-yl)-4-difluoromethoxy-8-methanesulfoneamide-dibenzo[b,d]furan-1-carboxamide comprising the steps of: (a) reacting 4-difluoromethoxy-3-hydroxybenzaldehyde with 2-bromo-1-fluoro-4-nitrobenzene in a first solvent comprising potassium fluoride to produce 4-difluoromethoxy-3-(4-nitro-2-bromophenoxy)benzaldehyde; (b) cyclizing 4-difluoromethoxy-3-(4-nitro-2-bromophenoxy)benzaldehyde in a second solvent comprising a catalyst to produce 4-difluoromethoxy-8-nitro-1-formyl dibenzofuran; (c) oxidizing 4-difluoromethoxy-8-nitro-1-formyl dibenzofuran in a third solvent comprising an oxidizing agent to produce 4-difluoromethoxy-8-nitrobenzo[b,d]furan-1-carboxylic acid; (d) reacting 4-difluoromethoxy-8-nitrobenzo[b,d]furan-1-carboxylic acid in a fourth solvent comprising an inorganic acid halide, 4-amino-3,5-dichloropyridine and a first base, wherein N-(3,5-dichloropyrid-4-yl)-4-difluoromethoxy-8-nitro-dibenzo[b,d]furan-1-carboxamide is produced; (e) reducing N-(3,5-dichloropyrid-4-yl)-4-difluoromethoxy-8-nitro-dibenzo[b,d]furan-1-carboxamide in the presence of a reducing agent to produce N-(3,5-dichloropyrid-4-yl)-4-difluoromethoxy-8-aminodibenzo[b,d]furan-1-carboxamide; and (f) reacting N-(3,5-dichloropyrid-4-yl)-4-difluoromethoxy-8-aminodibenzo[b,d]furan-1-carboxamide in a fifth solvent comprising methanesulfonyl chloride and a second base to produce N-(3,5-dichloropyrid-4-yl)-4-difluoromethoxy-8-(methanesulfonamide) dibenzo[b,d]furan-1-carboxamide.

DETAILED DESCRIPTION

Figure 1:
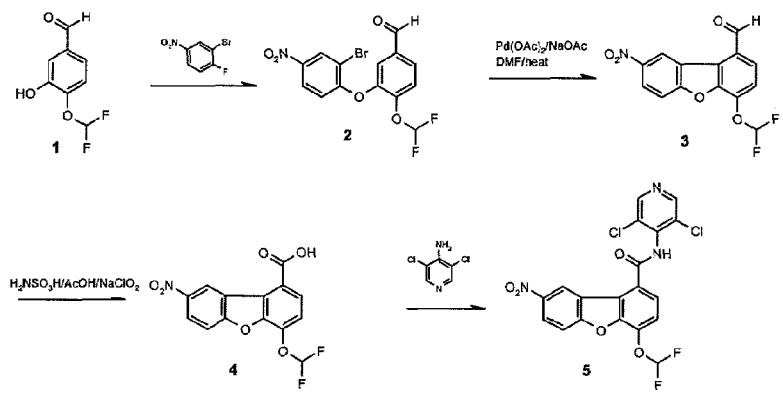
FIG. 1 shows an exemplary method for the synthesis of heterocyclic compounds according to the present invention.
Figure 1:
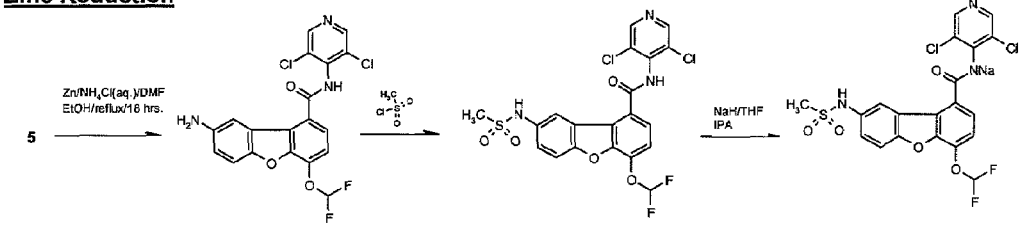
Figure 1:
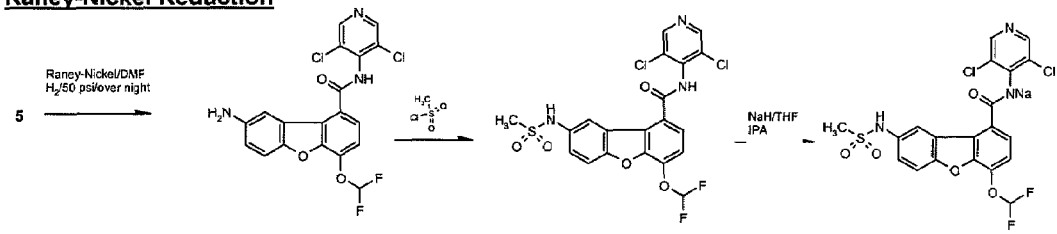
Figure 1:
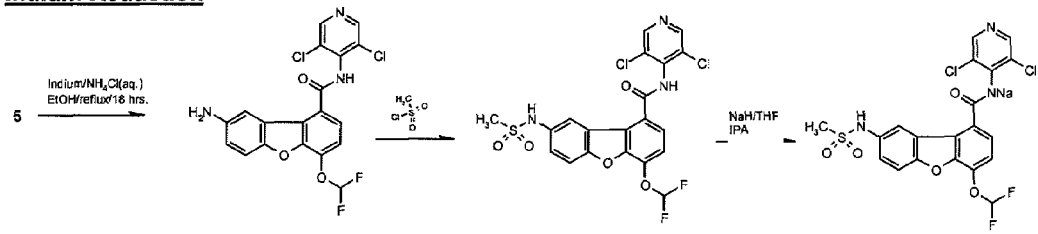

The present invention relates to methods for the synthesis of heterocyclic compounds including N-(3,5-dichloropyrid-4-yl)-4-difluoromethoxy-8-methanesulfonamido-dibenzo[b,d]furan-1-carboxamide and pharmaceutically acceptable salts thereof.

As used herein the term "alkyl" means a substituted or unsubstituted aliphatic hydrocarbon which may be straight or branched and may comprise 1 to 20 carbon atoms. Preferably the alkyl group contains 1 to 12 carbon atoms. More preferably the alkyl group contains 1 to 6 carbon atoms. Exemplary substituted alkyls include, but are not limited to, haloalkyl, heteroalkly and arylalkyl groups.

The term "halogen" means either Cl, Br, I or F.

The term "substituted" means that one or more of the atoms have been replaced by one or more substituents.

In one embodiment, a substituted nitrophenoxy benzaldehyde of formula (c) is formed by reacting a substituted benzaldehyde of formula (a) with a substituted nitrobenzene of formula (b) as shown in scheme I:

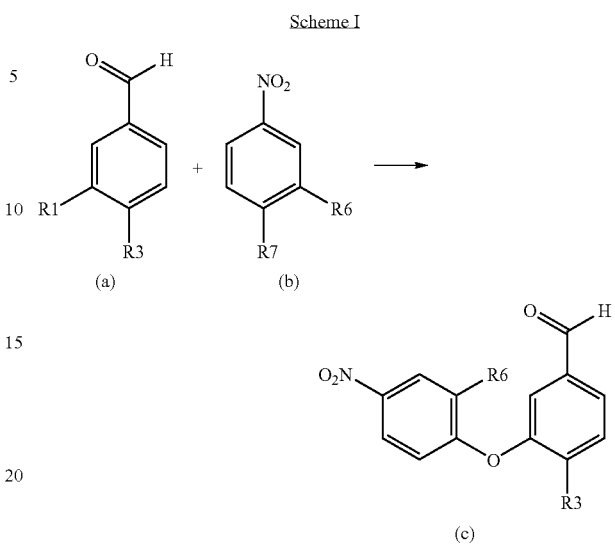

Scheme I wherein R1 is selected from the group consisting of O, OH, and OR2; R2 is a substituted or unsubstituted alkyl; R3 is selected from the group consisting of H, OH, halogen, and O—CHR4R5, wherein R4 and R5 are each independently selected from the group consisting of H, OH, and halogen; and R6 and R7 are each independently selected from the group consisting of H, OH, and halogen.

In exemplary embodiments, the substituted benzaldehyde of formula (a) is 4-difluoromethoxy-3-hydroxybenzaldehyde. In other exemplary embodiments, the substituted nitrobenzene of formula (b) is 2-bromo-1-fluoro-4-nitrobenzene. In further embodiments, the substituted nitrophenoxy benzaldehyde of formula (c) produced using scheme I is 4-difluoromethoxy-3-(4-nitro-2-bromophenoxy)benzaldehyde.

The reactions of scheme I may be performed in the presence of an organic solvent. Exemplary organic solvents include, but are not limited to, chlorinated solvents, aromatic solvents, alcoholic solvents, diethyl ether, 1,2-dimethoxyethane, tetrahydrofuran, diisopropyl ether, and 1,4-dioxane. Suitable chlorinated solvents include, but are not limited to, dichloromethane, 1,2-dichloroethane, chloroform, and carbon tetrachloride. Suitable aromatic solvents include, but are not limited to, benzene and toluene. Suitable alcoholic solvents include, but are not limited to, methanol, ethanol, n-propanol, isopropanol, and tert-butanol. Suitable polar aprotic solvents include, but are not limited to, N,N-dimethylformamide and dimethyl sulfoxide. In preferred embodiments, the reaction may be performed using dimethylformamide, dimethyl sulfoxide, tetrahydrofuran or dioxane.

The reactions of scheme I may also be performed in the presence of an alkali halide salt. For example, the alkali halide salts include, but are not limited to, KF, KBr, KCL, KI, NaF, NaBr, NaCl, NaI, LiF, Cl, LiBr, and LiI. In preferred embodiments, the alkali halide salt is potassium fluoride.

The reactions of scheme I may also be performed in the presence of an inorganic base, such as, but not limited to, sodium carbonate.

The present invention also includes compounds of formula I and physiologically acceptable salts thereof

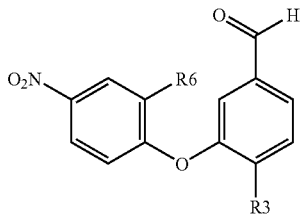

wherein R3 is selected from the group consisting of H, OH, halogen, and O—CHR4R5, wherein R4 and R5 are each independently selected from the group consisting of H and halogen; and R6 is selected from the group consisting of H, OH, and halogen. In preferred embodiments, the compound of formula I is 4-difluoromethoxy-3-(4-nitro-2-bromophenoxy)benzaldehyde.

In other exemplary embodiments, a substituted dibenzofuran of formula (d) is prepared by cyclization of a substituted nitrophenoxy benzaldehyde of formula (c) as shown in scheme II:

Scheme II

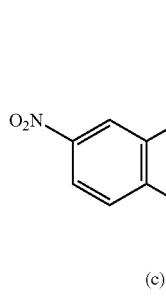

(c)

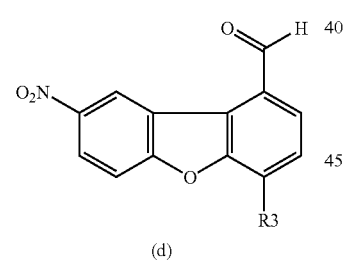

(d)

wherein R3 is selected from the group consisting of H, OH, halogen, and O—CHR4R5, wherein R4 and R5 are each independently selected from the group consisting of H, OH and halogen; and R6 is selected from the group consisting of H, OH, and halogen.

In exemplary embodiments, the substituted nitrophenoxy benzaldehyde of formula (c) is 4-difluoromethoxy-3-(4-nitro-2-bromophenoxy)benzaldehyde. In further exemplary embodiments, the substituted dibenzofuran of formula (d) is 4-difluoromethoxy-8-nitro-1-formyl dibenzofuran.

The reaction of scheme II may be performed in the presence of a catalyst. Suitable catalysts include, but are not limited to, hydrogenation catalysts such as reactivated Raney Nickel, Pearlmans catalyst (palladium hydroxide), and Pd/C. In exemplary embodiments, the catalyst is a transition metal complex, such as a palladium complex. For example, palladium catalysts include, but are not limited to, Pd(II) complexes such as palladium acetate.

The reactions of scheme II may be performed in the presence of an organic solvent. Exemplary organic solvents include, but are not limited to, chlorinated solvents, aromatic solvents, alcoholic solvents, diethyl ether, 1,2-dimethoxyethane, tetrahydrofuran, diisopropyl ether, and 1,4-dioxane. Suitable chlorinated solvents include, but are not limited to, dichloromethane, 1,2-dichloroethane, chloroform, and carbon tetrachloride. Suitable aromatic solvents include, but are not limited to, benzene and toluene. Suitable alcoholic solvents include, but are not limited to, methanol, ethanol, n-propanol, isopropanol, and tert-butanol. Suitable polar aprotic solvents include, but are not limited to, N,N-dimethylformamide and dimethyl sulfoxide. In preferred embodiments, the reaction may be performed using dimethylformamide, dimethyl sulfoxide, tetrahydrofuran or dioxane.

In one embodiment, the substituted dibenzofuran of formula (d) may be prepared according to schemes I and II without isolating the substituted nitrophenoxy benzaldehyde of formula (c).

In another embodiment, a substituted carboxylic acid of formula (e) is formed by oxidizing a substituted dibenzofuran of formula (d) as shown in scheme III:

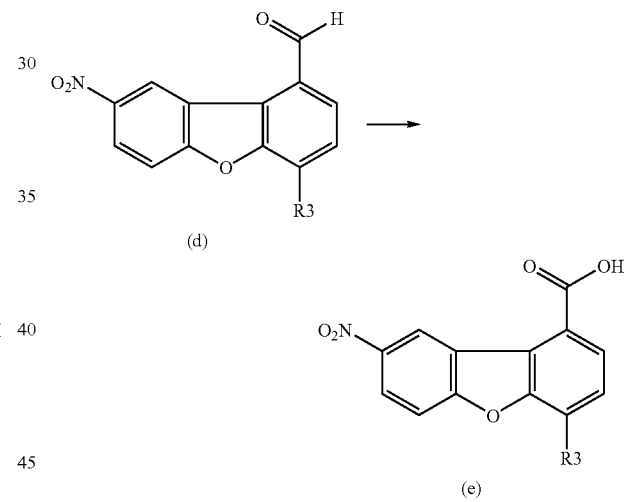

wherein R3 is selected from the group consisting of H, OH, halogen, and O—CHR4R5, wherein R4 and R5 are each independently selected from the group consisting of H, OH and halogen.

In exemplary embodiments, the substituted dibenzofuran of formula (d) is 4-difluoromethoxy-8-nitro-1-formyl dibenzofuran. In further exemplary embodiments, the substituted carboxylic acid of formula (e) is 4-difluoromethoxy-8-nitrobenzo[b,d]furan-1-carboxylic acid.

The reaction of scheme III may be performed in the presence of an oxidizing agent. For example, oxidizing agents may include, but are not limited to, potassium permanganate, sulfamic acid, sodium chlorite, hydrogen peroxide, silver oxide, rutenium chloride and combinations thereof. In some embodiments, the oxidizing agent may be a combination of sulfamic acid and sodium chlorite. In further embodiments the sulfamic acid to sodium chlorite is in a ratio between approximately 1:2 and approximately 2:1, preferably, a ratio between approximately 2:3 and approximately 3:2.

The reactions of scheme III may be performed in the presence of an organic solvent. Exemplary organic solvents include, but are not limited to, chlorinated solvents, aromatic solvents, alcoholic solvents, diethyl ether, 1,2-dimethoxyethane, tetrahydrofuran, diisopropyl ether, and 1,4-dioxane. Suitable chlorinated solvents include, but are not limited to, dichloromethane, 1,2-dichloroethane, chloroform, and carbon tetrachloride. Suitable aromatic solvents include, but are not limited to, benzene and toluene. Suitable alcoholic solvents include, but are not limited to, methanol, ethanol, n-propanol, isopropanol, and tert-butanol. Suitable polar aprotic solvents include, but are not limited to, N,N-dimethylformamide and dimethyl sulfoxide. In preferred embodiments, the reaction may be performed the presence of a polar solvent. For example, the polar solvent may be glacial acetic acid.

In other embodiments, a substituted carboxamide of formula (g) may be prepared by reacting a substituted carboxylic acid of formula (e) with a substituted aminopyridine of formula (f) as shown in scheme IV:

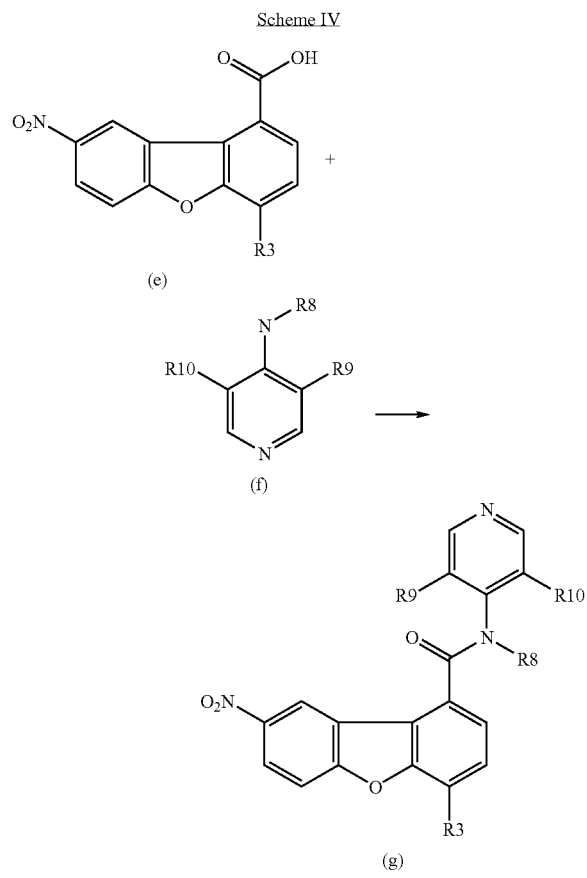

wherein R3 is selected from the group consisting of H, OH, halogen, and O—CHR4R5, wherein R4 and R5 are each independently selected from the group consisting of H, OH and halogen; R8 is selected from the group consisting of H and alkyl; and R9 and R10 are each independently selected from the group consisting of H, OH and halogen.

In exemplary embodiments, the substituted carboxylic acid of formula (e) is 4-difluoromethoxy-8-nitrobenzo[b,d]furan-1-carboxylic acid. In other exemplary embodiments, the substituted aminopyridine of the formula (f) is 4-amino-3,5-dichloropyridine. In further exemplary embodiments, the substituted carboxamide of formula (g) is N-(3,5-dichloropyrid-4-yl)-4-difluoromethoxy-8-nitro-dibenzo[b,d]furan-1-carboxamide.

The reaction of scheme IV may be performed in the presence of an inorganic acid halide. For example, inorganic acid halides that may be used include, but are no limited to, thionyl chloride, phosphorus trichloride, phosphorus pentachloride, thionyl chloride in presence of a catalytic amount of dimethylformamide, and pyridine. In some embodiments, the inorganic acid halide is thionyl chloride in the presence of a catalytic amount of dimethylformamide. In some embodiments, the reaction of scheme IV may be performed in the presence of a base. For example, the base may include, but is not limited to, potassium tertiary butoxide, sodium tertiary butoxide, and lithium tertiary butoxide.

In other embodiments, the present invention provides methods of preparing N-(3,5-dichloropyrid-4-yl)-4-difluoromethoxy-8-methanesulfonamide-dibenzo[b,d]furan-1-carboxamide, as shown in FIG. 1. For example, 4-difluoromethoxy-3-hydroxybenzaldehyde may be reacted with 2-bromo-1-fluoro-4-nitrobenzene in a first solvent comprising potassium fluoride to produce 4-difluoromethoxy-3-(4-nitro-2-bromophenoxy)benzaldehyde (scheme I). In a second step, the 4-difluoromethoxy-3-(4-nitro-2-bromophenoxy)benzaldehyde may be cyclized in a second solvent comprising a catalyst to produce 4-difluoromethoxy-8-nitro-1-formyl dibenzofuran (scheme II). In a third step, the 4-difluoromethoxy-8-nitro-1-formyl dibenzofuran may be oxidized in a third solvent comprising an oxidizing agent to produce 4-difluoromethoxy-8-nitrobenzo[b,d]furan-1-carboxylic acid (scheme III). In a fourth step, 4-difluoromethoxy-8-nitrobenzo[b,d]furan-1-carboxylic acid may be reacted in a fourth solvent comprising an inorganic acid halide, 4-amino-3,5-dichloropyridine and a first base to produce N-(3,5-dichloropyrid-4-yl)-4-difluoromethoxy-8-nitro-dibenzo[b,d]furan-1-carboxamide (scheme IV). In a fifth step, N-(3,5-dichloropyrid-4-yl)-4-difluoromethoxy-8-nitro-dibenzo[b,d]furan-1-carboxamide may be reduced in the presence of a reducing agent to produce N-(3,5-dichloropyrid-4-yl)-4-difluoromethoxy-8-aminodibenzo[b,d]furan-1-carboxamide. Suitable reducing agents include, but are not limited to, zinc, indium, iron, tin, Raney-nickel and sodium borohydride. In a sixth step, the N-(3,5-dichloropyrid-4-yl)-4-difluoromethoxy-8-aminodibenzo[b,d]furan-1-carboxamide may be reacted in a fifth solvent comprising methanesulfonyl chloride and a second base to produce N-(3,5-dichloropyrid-4-yl)-4-difluoromethoxy-8-(methanesulfonamide)dibenzo[b,d]furan-1-carboxamide.

The solvent used in the fifth step may include organic solvents such as, but not limited to, chlorinated solvents, aromatic solvents, alcoholic solvents, diethyl ether, 1,2-dimethoxyethane, tetrahydrofuran, diisopropyl ether, and 1,4-dioxane. Suitable chlorinated solvents include, but are not limited to, dichloromethane, 1,2-dichloroethane, chloroform, and carbon tetrachloride. Suitable aromatic solvents include, but are not limited to, benzene and toluene. Suitable alcoholic solvents include, but are not limited to, methanol, ethanol, n-propanol, isopropanol, and tert-butanol. Suitable polar aprotic solvents include, but are not limited to, N,N-dimethylformamide and dimethyl sulfoxide. In some embodiments, the reaction may be performed the presence of tetrahydrofuran, dioxane and toluene. In preferred embodiments, the solvent is tetrahydrofuran. The base used in the fifth step may include, but is not limited to, potassium tertiary butoxide, sodium tertiary butoxide, lithium tertiary butoxide, pyridine, 2,6-lutidine and triethylamine. In preferred embodiments, the base is pyrridine.

In yet other embodiments, the N-(3,5-dichloropyrid-4-yl)-4-difluoromethoxy-8-(methanesulfonamide)dibenzo[b,d]furan-1 is reacted in a sixth solvent comprising sodium hydride to produce N-(3,5-dichloropyrid-4-yl)-4-difluoromethoxy-8-(methanesulfonamide)dibenzo[b,d]furan-1-carboxamide sodium salt, as shown in FIG. 1. The solvent used to form the sodium salt may include organic solvents such as, but are not limited to, chlorinated solvents, aromatic solvents, alcoholic solvents, diethyl ether, 1,2-dimethoxyethane, tetrahydrofuran, diisopropyl ether, and 1,4-dioxane. Suitable chlorinated solvents include, but are not limited to, dichloromethane, 1,2-dichloroethane, chloroform, and carbon tetrachloride. Suitable aromatic solvents include, but are not limited to, benzene and toluene. Suitable alcoholic solvents include, but are not limited to, methanol, ethanol, n-propanol, isopropanol, and tert-butanol. Suitable polar aprotic solvents include, but are not limited to, N,N-dimethylformamide and dimethyl sulfoxide. In some embodiments, the reaction may be performed the presence of tetrahydrofuran, dioxane and toluene. In preferred embodiments, the solvent is tetrahydrofuran.

The present invention provides enhanced synthetic routes to produce heterocyclic compounds with high quality and in high yield. For example, the present invention provides novel methods for the synthesis of N-(3,5-dichloropyrid-4-yl)-4-difluoromethoxy-8-methanesulfonamido-dibenzo[b,d]furan-1-carboxamide and N-(3,5-dichloropyrid-4-yl)-4-difluoromethoxy-8-methanesulfonamido-dibenzo[b,d]furan-1-carboxamide sodium salt. In some embodiments, the invention may be used to produce heterocyclic compounds with a purity of at least 95%, preferably 98% and more preferably 99%. Thus, the present invention provides methods to produce pharmaceutical grade products that are suitable for being formulated into pharmaceutical compositions.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Example 1

Preparation of 4-difluoromethoxy-3-(4-nitro-2-bromophenoxy)benzaldehyde 4-difluoromethoxy-3-(4-nitro-2-bromophenoxy)benzaldehyde was produced by reacting 4-difluoromethoxy-3-hydroxybenzaldehyde with 2-bromo-1-fluoro-4-nitrobenzene in DMSO in the presence of potassium fluoride. To a 1 L 3-neck round bottom flask, fitted with a mechanical stirrer and reflux condenser was added 4-difluoromethoxy-3-hydroxybenzaldehyde (48.05 g, 255.41 mmol), potassium fluoride (29.68 g, 510.82 mmol), 2-bromo-1-fluoro-4-nitrobenzene (56.75 g, 257.96 mmol) and dimethyl sulfoxide (384 mL). The reaction mixture was heated to 90° C. for 2 h (or until HPLC showed completion). The reaction was cooled to room temperature then added drop wise to ice-cold water (15 L) while stirring. Stirring was maintained for 1 h at room temperature. The precipitated product was filtered, washed with water (15 L). The product was dried in a vacuum oven at 65° C. overnight to yield a yellow solid (97.0 g, 97.9%). Purity 99.54% by HPLC. CHN calculated % C 43.33, % H 2.08, % N 3.61; observed % C 43.18, % H 1.76, % N 3.57.

Example 2

Preparation of 4-difluoromethoxy-8-nitro-1-formyl dibenzofuran 4-difluoromethoxy-8-nitro-1-formyl dibenzofuran was produced by reacting 4-difluoromethoxy-3-(4-nitro-2-bromophenoxy)benzaldehyde (prepared using the procedure of Example 1) with catalytic palladium acetate in DMF in the presence of sodium acetate. To a 1 L 3-neck round bottom flask, fitted with a mechanical stirrer and reflux condenser was added 4-difluoromethoxy-3-(4-nitro-2-bromophenoxy)benzaldehyde (92.50 g, 238.33 mmol), sodium acetate (29.33 g, 357.50 mmol) and dimethyl formamide (555.0 mL) with stirring. The reaction mixture was heated to 110-115° C. after which palladium acetate (1.34 g, 5.96 mmol) was added and the temperature maintained at 110-115° C. for 1 h. After this time, a second portion of palladium acetate (1.34 g, 5.96 mmol) was added and stirred for an additional 1 h. An additional six portions of palladium acetate (each 1.34 g, 5.96 mmol) were added to the reaction mixture every hour while monitoring the reaction by HPLC. The reaction mixture was cooled to 60° C., filtered through celite and washed with DMF. The filtrate was added drop wise to a stirred vessel of water over 30-60 minutes. The precipitates were filtered, washed with water (500 mL) and dried in a vacuum oven (70° C.). The crude aldehyde was recrystallized with acetic acid (800 mL), the solid was filtered and washed with acetic acid (70 mL), heptane (500 mL) and dried in a vacuum oven (65-70° C.). The dried product appeared as a tan solid (51.07 g, 71.1%). Purity 93.46% by HPLC. $^1$H NMR (500 MHz, DMSO-$d_6$): 7.68 (t, J=72.3 Hz, 1H), 7.78 (d, J=8.5 Hz, 1H), 8.11 (d, J=9.5 Hz, 1H), 8.26 (d, J=8.0 Hz, 1H), 8.55 (dd, J=2.5, 9.0 Hz, 1H), 9.78 (d, J=2.5 Hz, 1H), 10.28 (s, 1H) ppm.

Example 2A

Preparation of 4-difluoromethoxy-8-nitro-1-formyl dibenzofuran 4-difluoromethoxy-8-nitro-1-formyl dibenzofuran was produced by reacting 4-difluoromethoxy-3-hydroxybenzaldehyde with 2-bromo-1-fluoro-4-nitrobenzene in DMF in the presence of sodium carbonate, followed by the reaction with catalytic palladium acetate in the presence of sodium acetate. To a 100 mL 3-neck round bottom flask, fitted with a mechanical stirrer and reflux condenser was added 4-difluoromethoxy-3-hydroxybenzaldehyde (7.525 g, 40 mmol), sodium carbonate (2.544 g, 24 mmol), 2-bromo-1-fluoro-4-nitrobenzene (8.89 g, 40 mmol) and dimethyl formamide (DMF, 60 mL). The reaction mixture was heated to 90° C. for 2 h. To this were added sodium acetate (4.92 g, 60 mmol) and palladium acetate (0.898 g, 4 mmol) with stirring. The reaction mixture was heated to 130° C. and the temperature maintained at 125-130° C. for 1 h. After this time, a second portion of palladium acetate (0.45 g, 2 mmol) was added and stirred for an additional 1 h. The reaction mixture was cooled to room temperature, filtered through celite and washed with DMF. The filtrate was added drop wise to a stirred vessel of water over 30-60 minutes. The precipitates were filtered, washed with water (50 mL) and dried in a vacuum oven (70° C.). The crude aldehyde was recrystallized with acetic acid (800 mL), the solid was filtered and washed with acetic acid (20 mL) and dried in a vacuum oven (65-70° C.). The dried product appeared as a tan solid (8.24 g, 67%).

Example 3

Preparation of 4-difluoromethoxy-8-nitrobenzo[b,d]furan-1-carboxylic acid 4-difluoromethoxy-8-nitrobenzo[b,d]furan-1-carboxylic acid was prepared by oxidizing 4-difluoromethoxy-8-nitro-1-formyl dibenzofuran (prepared using the procedure of Example 2) in sulfamic acid, glacial acetic acid and sodium chlorite. To a 2 L 3-neck round bottom flask, fitted with a mechanical stirrer was added 4-difluoromethoxy-8-nitro-1-formyl dibenzo[b,d]furan (51.00 g, 166.01 mmol), sulfamic acid (48.35 g, 498.03 mmol), glacial acetic acid (510.0 mL) and stirred at room temperature. To this mixture was added sodium chlorite (45.05 g, 498.03 mmol) in portions (slight exotherm). The reaction was stirred at room temperature for 50 minutes (reaction monitored by HPLC). Additional sodium chlorite (16.12 g, 178.24 mmol) was added to the reaction and stirred at room temperature until HPLC indicated completion of the reaction. Water (1.53 L) was added to the reaction mixture and stirred for 30-60 minutes. The precipitated solid was filtered, washed with water (350 mL), heptane (350 mL) and dried in vacuum oven (65° C.) overnight. The dried product appeared as a yellow solid (51.27 g, 97.8%). Purity 95.61% by HPLC; $^1$H NMR (500 MHz, DMSO-$d_6$): 7.61 (t, J=72.5 Hz, 1H), 7.62 (d, J=8.5 Hz, 1H), 8.07 (d, J=9.0 Hz, 1H), 8.12 (d, J=8.5 Hz, 1H), 8.52 (dd, J=2.5, 9.0 Hz, 1H), 9.77 (d, J=2.5 Hz, 1H), 13.73 (bs, 1H) ppm.

Example 4

Preparation of N-(3,5-dichloropyrid-4-yl)-4-difluoromethoxy-8-nitro-dibenzo[b,d]furan-1-carboxamide N-(3,5-dichloropyrid-4-yl)-4-difluoromethoxy-8-nitrodibenzo[b,d]furan-1-carboxamide was prepared by reacting 4-difluoromethoxy-8-nitrobenzo[b,d]furan-1-carboxylic acid (prepared using the procedure of Example 3) with thionyl chloride and dimethyl formamide in toluene. To a 1 L 3-neck round bottom flask, fitted with a mechanical stirrer and reflux condenser was added 4-difluoromethoxy-8-nitrobenzo[b,d]furan-1-carboxylic acid (34.00 g, 105.19 mmol), toluene (510.0 mL), thionyl chloride (38.3 mL, 525.95 mmol) and catalytic dimethyl formamide (2.6 mL). The reaction mixture was heated to 80-90° C. for 2-2.5 h. After ascertaining completion of the reaction, the reaction mixture was concentrated in vacuo at 55-60° C. to give the acid chloride as a yellow solid. Dimethyl formamide (140 mL) was added to the acid chloride and used without further purification in the following coupling step. A 1 L 3-neck round bottom flask, fitted with a mechanical stirrer was added 4-amino-3,5-dichloropyridine (34.30 g, 210.39 mmol) and dimethyl formamide (680.00 mL). Potassium tert-butoxide (23.61 g, 210.39 mmol) was added to the reaction mixture and stirred at room temperature for 0.5-1 h. The acid chloride solution, prepared earlier, was added drop wise to the potassium salt suspension whilst stirring vigorously, maintaining the temperature below 30° C. The reaction was stirred at room temperature until HPLC indicated the reaction was complete. Water (2.04 L) was added to the reaction mixture, the pH adjusted to 2-3 with concentrated hydrochloric acid. The precipitate was filtered, washed with water (200 mL) and resuspended in a solution of water (2 L) and acetonitrile (170 mL). The pH was adjusted to 10 with 2N NaOH (7.6 mL) solution followed by heating to 63-67° C. for 0.5-1 h. The mixture was cooled to room temperature, the solid was filtered, washed with water (200 mL) and dried in a vacuum oven (65° C.) overnight. The crude amide was recrystallized from boiling acetic acid (2.42 L) and DMF (33 mL). The product was filtered, washed with acetic acid (132.0 mL), heptane (264.0 mL) and dried in a vacuum oven (65° C.) overnight. The product appeared as an off-white solid (32.49 g, 74.28%). Purity 97.94% by HPLC; m/z 467.68 (M$^+$).

Example 5

Reduction of N-(3,5-dichloropyrid-4-yl)-4-difluoromethoxy-8-nitro-dibenzo[b,d]furan-1-carboxamide N-(3,5-dichloropyrid-4-yl)-4-difluoromethoxy-8-aminodibenzo[b,d]furan-1-carboxamide was prepared using four separate reduction routes.

First, N-(3,5-dichloropyrid-4-yl)-4-difluoromethoxy-8-aminodibenzo[b,d]furan-1-carboxamide was prepared by reacting N-(3,5-dichloropyrid-4-yl)-4-difluoromethoxy-8-nitro-dibenzo[b,d]furan-1-carboxamide (prepared using the procedure of Example 4) with indium in ethanol and saturated ammonium chloride. To a 1 L 3-neck round bottom flask, fitted with a mechanical stirrer and reflux condenser was added N-(3,5-dichloropyrid-4-yl)-4-difluoromethoxy-8-nitro-dibenzo[b,d]furan-1-carboxamide (22.00 g, 46.99 mmol), ethanol (308.0 mL), sat. aq. NH$_4$Cl (132.0 mL) and indium (32.37 g, 281.93 mmol). The reaction mixture was heated to 80° C. for 4-5 h (reaction monitored by HPLC). Additional indium (5.40 g, 47.03 mmol) was added to the reaction and heated to 80° C. until HPLC indicated completion. After cooling to room temperature the reaction was evaporated to dryness. DMF (200 mL) was added to the solids and heated to 70-75° C. The solution was filtered, washed with DMF (100 mL) and concentrated to a volume of 50 mL in vacuo. Water (3 L) was added to the reaction mixture, the solid was filtered, washed with water (66 mL) and dried in a vacuum oven (65° C.) overnight. The dried product appeared as a yellow solid (17.77 g, 77.4%). Purity 87.84% by HPLC; $^1$H NMR (500 MHz, DMSO-$d_6$): 5.11 (bs, 2H), 6.86 (dd, J=2.3, 8.8 Hz, 1H), 7.46-7.51 (m, 3H), 7.53 (t, J=73.0 Hz, 1H), 7.82 (d, J=8.0 Hz, 1H), 8.80 (s, 2H), 10.93 (bs, 1H) ppm. m/z 437.1 (M$^+$).

Second, N-(3,5-dichloropyrid-4-yl)-4-difluoromethoxy-8-aminodibenzo[b,d]furan-1-carboxamide was prepared by reacting N-(3,5-dichloropyrid-4-yl)-4-difluoromethoxy-8-nitro-dibenzo[b,d]furan-1-carboxamide (prepared using the procedure of Example 4) with Raney Nickel. In particular, to a 500 mL pressure vessel was added N'-(3,5-dichloropyrid-4-yl)-4-difluoromethoxy-8-nitro-dibenzo[b,d]furan-1-carboxamide (2.00 g, 4.27 mmol), DMF (30.0 mL) and Raney Nickel (1.79 g). The reaction mixture was hydrogenated (50 psi) for 23 h (reaction monitored by HPLC). The reaction mixture was filtered, washed with DMF (20 mL) and the filtrate concentrated to a 5 mL volume (distilled below 70° C. under vacuum). Water (33.0 mL) was added, the precipitate filtered, washed with water (20 mL) and dried in a vacuum oven (65° C.) to yield the amine as a cream colored solid (1.67 g, 91.3%). Purity 98.67% by HPLC.

Third, N-(3,5-dichloropyrid-4-yl)-4-difluoromethoxy-8-aminodibenzo[b,d]furan-1-carboxamide was prepared by reacting N-(3,5-dichloropyrid-4-yl)-4-difluoromethoxy-8-nitro-dibenzo[b,d]furan-1-carboxamide (prepared using the procedure of Example 4) with zinc. In particular, to a 250 mL 2-necked round bottom flask was added N'-(3,5-dichloropyrid-4-yl)-4-difluoro methoxy-8-nitro-dibenzo[b,d]furan-1-carboxamide (1.00 g, 2.14 mmol), sat.aq. ammonium chloride (30.0 mL), ethanol (10.0 mL) and zinc (0.84 g, 12.82 mmol). The reaction mixture was heated to 95° C. over the weekend. The solvent was removed in vacuo, DMF (14 mL) was added to the residue and heated to 50-55° C. until dissolution. The hot solution was filtered, washed with DMF (4 mL) and poured onto water (100 mL). The precipitate was filtered, washed with water (20 mL) and dried in a vacuum oven to yield the amine as a pale yellow solid (0.73 g, 79.4%). Purity 86.31% by HPLC.

Fourth, N-(3,5-dichloropyrid-4-yl)-4-difluoromethoxy-8-aminodibenzo[b,d]furan-1-carboxamide was prepared by reacting N-(3,5-dichloropyrid-4-yl)-4-difluoromethoxy-8-nitro-dibenzo[b,d]furan-1-carboxamide (prepared using the procedure of Example 4) with sodium borohydride in methanol and palladium on carbon (50% wet with water) catalyst. In particular, to a 100 mL 3-neck round bottom flask were added N-(3,5-dichloropyrid-4-yl)-4-difluoromethoxy-8-nitro-dibenzo[b,d]furan-1-carboxamide (0.468 g, 1 mmol), methanol (15.0 mL), and 10% Pd—C (50% wet, 0.012 g). The reaction mixture was cooled to 5-10° C. and treated with sodium borohydride (0.127 g, 4 mmol) in four portions. The reaction mixture was acidified with conc. HCl to pH~6, filtered and the Pd-C catalyst was washed with MeOH (~10 ml). The combined filtrate was concentrated to a residue and slurried in excess water. The solid was filtered, washed with water (75 mL) and dried in a vacuum oven (65° C.) overnight. The dried product appeared as a yellow solid (0.310 g, 70.7%). Purity 79.57% by HPLC.

Example 6

Preparation of N-(3,5-dichloropyrid-4-yl)-4-difluoromethoxy-8-(methanesulfonamide)dibenzo[b,d]furan-1

N-(3,5-dichloropyrid-4-yl)-4-difluoromethoxy-8-(methanesulfonamide)dibenzo[b,d]furan-1-carboxamide was prepared by reacting N-(3,5-dichloropyrid-4-yl)-4-difluoromethoxy-8-aminodibenzo[b,d]furan-1-carboxamide (prepared using the procedure of Example 5) with methanesulfonyl chloride in THF and pyridine. To a 1 L 4-neck round bottom flask, fitted with a mechanical stirrer and reflux condenser was added N-(3,5-dichloropyrid-4-yl)-4-difluoromethoxy-8-aminodibenzo[b,d]furan-1-carboxamide (17.00 g, 38.79 mmol) and THF (255 mL). Pyridine (12.5 mL) was added slowly to the mixture and allowed to stir for 15 minutes. Methanesulfonyl chloride (18.1 mL, 232.74 mmol) was added to the reaction mixture and stirred at room temperature until reaction completion as indicated by HPLC. 2 N HCl (34.0 mL) was added to the reaction mixture and stirred for 10-15 minutes. This mixture was added drop wise to water (1.7 L), the solid was filtered, washed with 2 N HCl (17.0 mL), water (51 mL) and methanol (51 mL). The crude product was recrystallized from hot acetic acid (700 mL) and the solids dried in a vacuum oven (65-70° C.) to yield the product as a cream colored solid (14.24 g, 81.1%). Purity 98.04% by HPLC; $^1$H NMR (500 MHz, DMSO-$d_6$): 2.94 (s, 3H), 7.52 (dd, J=2.0, 9.0 Hz, 1H), 7.58 (t, J=73.0 Hz, 1H), 7.62 (d, J=8.5 Hz, 1H), 7.84 (d, J=9.0 Hz, 1H), 7.93 (d, J=8.5 Hz, 1H), 8.31 (m, 1H), 8.82 (s, 2H), 9.76 (s, 1H), 11.04 (s, 1H) ppm; m/z 515.79 (M$^+$).

Example 7

Preparation of N-(3,5-dichloropyrid-4-yl)-4-difluoromethoxy-8-(methanesulfonamide)dibenzo[b,d]furan-1-carboxamide sodium salt N-(3,5-dichloropyrid-4-yl)-4-difluoromethoxy-8-(methanesulfonamide)dibenzo[b,d]furan-1-carboxamide sodium salt was prepared by reacting N-(3,5-dichloropyrid-4-yl)-4-difluoromethoxy-8-(methanesulfonamide)dibenzo[b,d]furan-1-carboxamide (prepared using the procedure of Example 6) with sodium hydride in THF. To a 500 mL 3-neck round bottom flask was added GRC-3845 (17.00 g, 32.93 mmol) and THF (170.0 mL) and cooled to 0-5° C. Sodium hydride (1.48 g, 36.88 mmol, 60% dispersed in mineral oil) was added slowly, maintaining the temperature between 0-5° C. The mixture was maintained at this temperature for 10 minutes and then warmed to room temperature. The mixture was diluted with THF (34.0 mL) and heated to reflux for 1-2 h. The solvent was removed in vacuo (temperature 40° C.). Isopropyl alcohol (102 mL) was added to the residue and the mixture heated to reflux for 3-4 h. The reaction was cooled to room temperature, filtered, washed with isopropyl alcohol (25 mL) and dried in a vacuum oven (70° C.) to yield the sodium salt as a pale yellow solid (16.33 g, 92.8%). Purity 99.6% by HPLC; m/z 515.80 (M$^+$).

Using the indium reduction described in example 5, 97.0 grams of starting material was converted to 44.9 grams of N-(3,5-dichloropyrid-4-yl)-4-difluoromethoxy-8-(methanesulfonamide)dibenzo[b,d]furan-1-carboxamide for a yield of 34.1% and 43.4 grams of -(3,5-dichloropyrid-4-yl)-4-difluoromethoxy-8-(methanesulfonamide)dibenzo[b,d]furan-1-carboxamide sodium salt for a yield of 31.6%. Using the Raney-nickel reduction described in example 5, 97.0 grams of starting material was converted to 53.1 grams of N-(3,5-dichloropyrid-4-yl)-4-difluoromethoxy-8-(methanesulfonamide)dibenzo[b,d]furan-1-carboxamide for a yield of 39.9% and 51.3 grams of -(3,5-dichloropyrid-4-yl)-4-difluoromethoxy-8-(methanesulfonamide)dibenzo[b,d]furan-1-carboxamide sodium salt for a yield of 37.0%. Using the zinc reduction described in example 5, 97 grams of starting material was converted to 36.8 grams of N-(3,5-dichloropyrid-4-yl)-4-difluoromethoxy-8-(methanesulfonamide)dibenzo[b,d]furan-1-carboxamide for a yield of 27.9% and 35.6 grams of -(3,5-dichloropyrid-4-yl)-4-difluoromethoxy-8-(methanesulfonamide)dibenzo[b,d]furan-1-carboxamide sodium salt for a yield of 25.9%.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects. All references cited herein are hereby incorporated by reference in their entirety.

We claim:

1. A method of preparing N-(3,5-dichloropyrid-4-yl)-4-difluoromethoxy-8-methanesulfonamide-dibenzo[b,d]furan-1-carboxamide comprising the steps of:
    (a) reacting 4-difluoromethoxy-3-hydroxybenzaldehyde with 2-bromo-1-fluoro-4-nitrobenzene in a first solvent in the presence of an potassium fluoride to produce 4-difluoromethoxy-3-(4-nitro-2-bromophenoxy)benzaldehyde;

(b) cyclizing 4-difluoromethoxy-3-(4-nitro-2-bromophenoxy)benzaldehyde in a second solvent in the presence of a catalyst to produce 4-difluoromethoxy-8-nitro-1-formyl dibenzofuran;

(c) oxidizing 4-difluoromethoxy-8-nitro-1-formyl dibenzofuran in a third solvent in the presence of an oxidizing agent to produce 4-difluoromethoxy-8-nitrobenzo[b,d]furan-1-carboxylic acid;

(d) reacting 4-difluoromethoxy-8-nitrobenzo[b,d]furan-1-carboxylic acid with 4-amino-3,5-dichloropyridine in a fourth solvent in the presence of an inorganic acid halide and a first base, to produce N-(3,5-dichloropyrid-4-yl)-4-difluoromethoxy-8-nitro-dibenzo[b,d]furan-1-carboxamide;

(e) reducing N-(3,5-dichloropyrid-4-yl)-4-difluoromethoxy-8-nitro-dibenzo[b,d]furan-1-carboxamide in the presence of a reducing agent to produce N-(3,5-dichloropyrid-4-yl)-4-difluoromethoxy-8-aminodibenzo[b,d]furan-1-carboxamide; and (f) reacting N-(3,5-dichloropyrid-4-yl)-4-difluoromethoxy-8-aminodibenzo[b,d]furan-1-carboxamide with methanesulfonyl chloride in a fifth solvent in the presence of and a second base to produce N-(3,5-dichloropyrid-4-yl)-4-difluoromethoxy-8-(methanesulfonamide) dibenzo[b,d]furan-1-carboxamide.

2. The method of claim 1, further comprising the step of reacting N-(3,5-dichloropyrid-4-yl)-4-difluoromethoxy-8-(methanesulfonamide)dibenzo[b,d]furan-1 with sodium hydride in a sixth solvent to produce N-(3,5-dichloropyrid-4-yl)-4-difluoromethoxy-8-(methanesulfonamide)dibenzo[b,d]furan-1-carboxamide sodium salt.

3. The method of claim 1, wherein the first solvent recited in step (a) comprises dimethyl sulfoxide.

4. The method of claim 1, wherein the catalyst recited in step (b) comprises a transition metal complex.

5. The method of claim 1, wherein the catalyst recited in step (b) comprises palladium acetate.

6. The method of claim 1, wherein the second solvent recited in step (b) is selected from the group consisting of dimethylformamide, dimethyl sulfoxide, tetrahydrofuran and dioxane.

7. The method of claim 1, wherein the oxidizing agent recited in step (c) is selected from the group consisting of potassium permanganate, sulfamic acid, sodium chlorite, hydrogen peroxide, silver oxide, ruthenium chloride and combinations thereof.

8. The method of claim 7, wherein the oxidizing agent comprises sulfamic acid and sodium chlorite.

9. The method of claim 8, wherein the sulfamic acid to sodium chlorite ratio is between about 1:2 to about 2:1.

10. The method of claim 8, wherein the sulfamic acid to sodium chlorite ratio is between about 2:3 to about 3:2.

11. The method of claim 1, wherein the third solvent recited in step (c) comprises glacial acetic acid.

12. The method of claim 1, wherein the inorganic acid halide is selected from the group consisting of thionyl chloride, phosphorus trichloride, phosphorus pentachloride, thionyl chloride and pyridine.

13. The method of claim 1, wherein the inorganic acid halide comprises thionyl chloride in the presence of a catalytic amount of dimethylformamide.

14. The method of claim 1, wherein the first base recited in step (d) is selected from the group consisting of potassium tertiary butoxide, sodium tertiary butoxide and lithium tertiary butoxide.

15. The method of claim 1, wherein the fourth solvent recited in step (d) is selected from the group consisting of toluene, xylene and tetrahydrofuran.

16. The method of claim 1, wherein the reducing agent recited in step (e) is selected from the group consisting of zinc, indium, iron, tin, Raney-nickel and sodium borohydride.

17. The method of claim 1, wherein the second base recited in step (f) is selected from the group consisting of pyridine, 2,6-lutidine and triethylamine.

18. The method of claim 1, wherein the fifth solvent recited in step (f) is selected from the group consisting of tetrahydrofuran, dioxane and toluene.

* * * * *